(12) United States Patent
Magari et al.

(10) Patent No.: US 12,318,235 B2
(45) Date of Patent: Jun. 3, 2025

(54) X-RAY IMAGING APPARATUS

(71) Applicant: Shimadzu Corporation, Kyoto (JP)

(72) Inventors: Yoshihide Magari, Kyoto (JP); Hiroshi Inoue, Kyoto (JP); Atsuo Saito, Kyoto (JP); Toru Hayakawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 350 days.

(21) Appl. No.: 18/105,603

(22) Filed: Feb. 3, 2023

(65) Prior Publication Data

US 2023/0277147 A1   Sep. 7, 2023

(30) Foreign Application Priority Data

Mar. 7, 2022   (JP) ................................ 2022-034702
Dec. 2, 2022   (JP) ................................ 2022-193787

(51) Int. Cl.
*A61B 6/03*      (2006.01)
*A61B 6/00*      (2024.01)

(52) U.S. Cl.
CPC .......... *A61B 6/4441* (2013.01); *A61B 6/4405* (2013.01); *A61B 6/4464* (2013.01); *A61B 6/56* (2013.01)

(58) Field of Classification Search
CPC ... A61B 6/4405; A61B 6/4441; A61B 6/4464; A61B 6/56
See application file for complete search history.

(56) References Cited

U.S. PATENT DOCUMENTS

| | | | | |
|---|---|---|---|---|
| 2010/0150317 | A1* | 6/2010 | Herrmann | F16L 3/18 378/194 |
| 2013/0289542 | A1* | 10/2013 | Nyman | H02G 11/02 606/1 |
| 2021/0145384 | A1* | 5/2021 | Daugirdas | A61B 6/4441 |

FOREIGN PATENT DOCUMENTS

| | | | | |
|---|---|---|---|---|
| CN | 102463575 A | * | 5/2012 | ........... A61B 6/4441 |
| CN | 114123055 A | * | 3/2022 | ........... A61B 6/4441 |
| JP | 2008086372 A | | 4/2008 | |
| JP | 2021166633 A | | 10/2021 | |
| WO | WO-2007132419 A2 | * | 11/2007 | ........... A61B 6/4441 |
| WO | WO-2008053402 A1 | * | 5/2008 | ............. A61B 6/035 |

OTHER PUBLICATIONS

English translation of CN 102463575 (Year: 2012).*
English translation of CN 114123055 (Year: 2022).*

* cited by examiner

*Primary Examiner* — Mark R Gaworecki
(74) *Attorney, Agent, or Firm* — Muir Patent Law, PLLC

(57) ABSTRACT

An X-ray imaging apparatus is provided with an X-ray source, a detector, a C-shaped arm, a hose for accommodating wiring, the hose including a base side portion and an opposite side portion, a base including a C-shaped arm support portion and a hose attachment portion to which the base side portion is rotatably attached, a biasing member for biasing the base side portion of the hose to rotate about the hose attachment portion in the first rotation direction outwardly away from the C-shaped arm, and an image processing unit.

20 Claims, 11 Drawing Sheets

Comparative Example

X-RAY IMAGING APPARATUS

CROSS-REFERENCE TO RELATED APPLICATIONS

The related application numbers JP2022-034702, entitled "X-Ray Imaging Apparatus," filed on Mar. 7, 2022, Yoshihide Magari, Hiroshi Inoue, Atsuo Saito, and JP2022-193787, entitled on "X-ray imaging apparatus," filed on Dec. 2, 2022, Yoshihide Magari, Hiroshi Inoue, Atsuo Saito, Toni Hayakawa, upon which this patent application is based, are hereby incorporated by reference in their entirety.

BACKGROUND OF THE INVENTION

Field of the Invention

The present invention relates to an X-ray imaging apparatus, and more particularly, to an X-ray source and a detector including a wiring accommodating hose.

Description of the Related Art

The following description sets forth the inventor's knowledge of related art and problems therein and should not be construed as an admission of knowledge in the prior art.

Conventionally, an X-ray imaging apparatus provided with a hose for accommodating wiring connected to an X-ray source and a detector is known. Such an apparatus is disclosed in, for example, Japanese Unexamined Patent Application Publication No. 2008-86372.

Japanese Unexamined Patent Application Publication No. 2008-86372 discloses an X-ray imaging apparatus provided with a hose for accommodating a plurality of cables (wiring), such as, e.g., a high-voltage cable for supplying a high voltage to an X-ray source and a signal line cable for taking out a signal detected by a detector. Japanese Unexamined Patent Application Publication No. 2008-86372 discloses an X-ray imaging apparatus provided with a C-shaped arm for supporting an X-ray source and a detector, a second support portion (C-shaped arm support portion) for rotatably supporting the C-shaped arm, a cable bridged between the C-shaped arm and the second support portion, and a hose accommodating the cable therein with one end fixed to the C-shaped arm and the other end fixed to the second support portion.

The second support portion is configured to support the intermediate portion of the C-shaped arm by sandwiching the intermediate portion from both sides thereof and to move the C-shaped arm back and forth along the arc of the C-shaped arm. That is, the C-shaped arm slides in the circumferential direction thereof with respect to the second support portion. The hose accommodating the cable has a hanging portion hanging downward. In the hose, one end is fixed to the C-shaped arm, and the other end is fixed to the second support portion.

Although not disclosed in Japanese Unexamined Patent Application Publication No. 2008-86372, the position of the one end of the hose fixed to the C-shaped arm changes as the C-shaped arm moves in the circumferential direction. Therefore, due to the change in the position of one end of the hose in accordance with the movements of the C-shaped arm at least in the circumferential direction, the hose may approach a subject placed on the top board. In this situation, since the hose may come into contact with the subject, it is desired to prevent the hose from coming into contact with the subject placed on the top board as the C-shaped arm moves at least in the circumferential direction.

SUMMARY OF THE INVENTION

The present invention has been made to solve the above-described problems, and an object of the present invention is to provide an X-ray imaging apparatus capable of suppressing a hose from contacting a subject placed on a top board in accordance with a movement of a C-shaped arm at least in a circumferential direction.

In order to attain the above-described object, the X-ray imaging apparatus according to one aspect of the present invention includes:
  an X-ray source;
  a detector configured to detect X-rays emitted from the X-ray source;
  a C-shaped arm configured to support the X-ray source and the detector;
  a hose configured to accommodate wiring connected to at least one of the X-ray source and the detector, the hose including a base side portion and an opposite side portion connected to the C-shaped arm on an opposite side of the base side portion;
  a base including a C-shaped arm support portion rotatably supporting the C-shaped arm and a hose attachment portion to which the base side portion of the hose is rotatably attached;
  a biasing unit configured to bias the base side portion of the hose to rotate about the hose attachment portion in a first rotation direction away from an outside of the C-shaped arm; and an image processing unit configured to generate an image based on a detection signal output from the detector.
  Here, the "C-shaped arm" refers to an arm having a substantially C-shape as viewed from the side and supporting an X-ray source on one end side and a detector on the other end side.

The X-ray imaging apparatus according to one aspect of the present invention is provided with, as described above, a hose including a base side portion, a hose attachment portion on which the base side portion of the hose is rotatably mounted, and a biasing unit for biasing the base side portion of the hose to rotate the base side portion in a first rotation direction away from the C-shaped arm about the hose attachment portion.

With this configuration, even in a case where the position of the opposite side portion of the hose connected to the C-shaped arm opposite to the base side portion is changed in accordance with at least the circumferential movements of the C-shaped arm, it is possible to prevent the distance between the hose and the subject placed on the top board from decreasing because the base end portion of the hose is biased to rotate in a first rotation direction outwardly away from the C-shaped arm by the biasing unit. Therefore, it is possible to prevent the hose from coming into contact with the subject placed on the top board in accordance with at least the circumferential movements of the C-shaped arm.

BRIEF DESCRIPTION OF THE DRAWINGS

The preferred embodiments of the present invention are shown by way of example, and not limitation, in the accompanying figures.

DETAILED DESCRIPTION OF THE PREFERRED EMBODIMENTS

In the following paragraphs, some preferred embodiments of the invention will be described by way of example and not limitation. It should be understood based on this disclosure that various other modifications can be made by those skilled in the art based on these illustrated embodiments.

Hereinafter, some embodiments in which the present invention is embodied will be described with reference to the attached drawings.

First Embodiment (Configuration of X-Ray Imaging Apparatus)

The configuration of an X-ray imaging apparatus 100 according to a first embodiment will be described with reference to FIG. 1 to FIG. 7.

Figure 1:
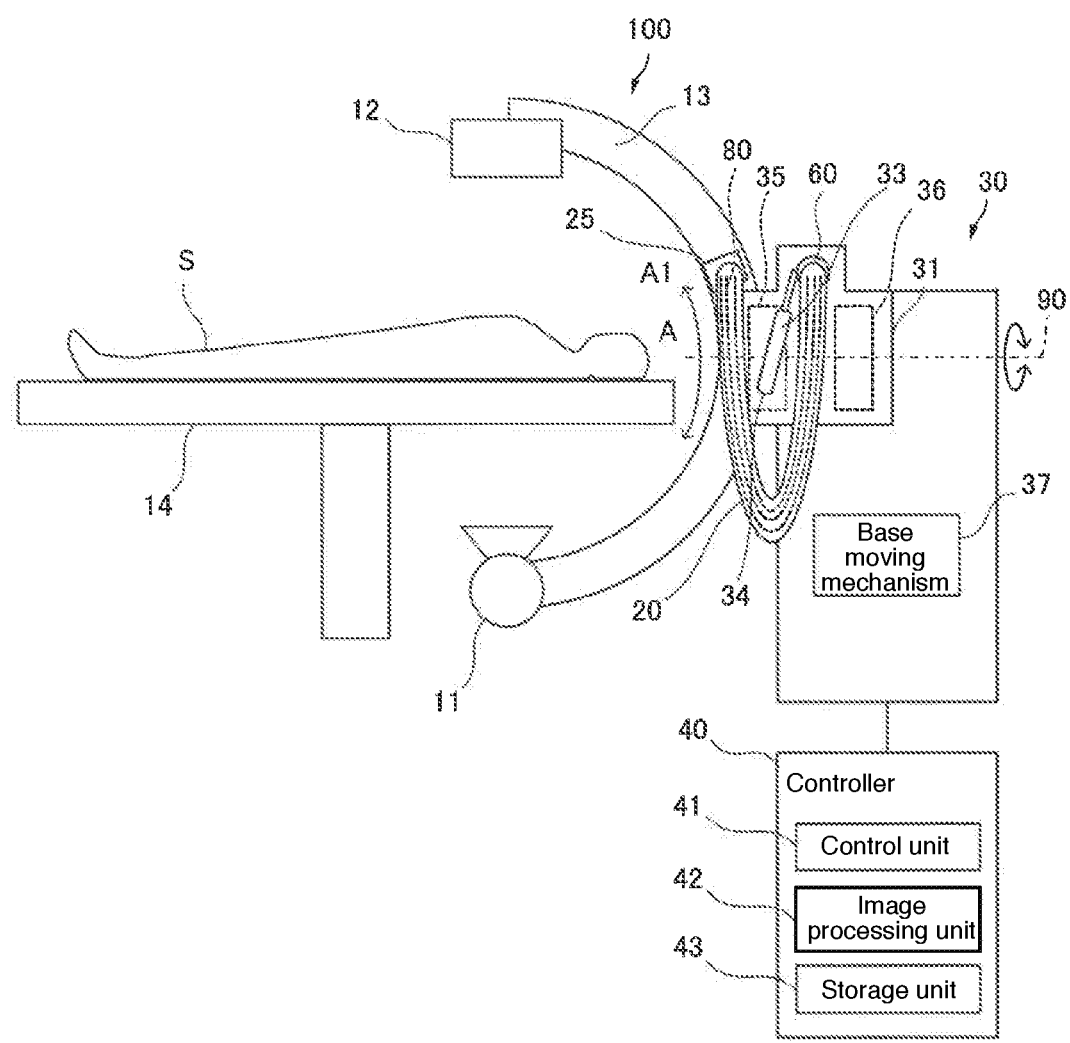
FIG. 1 is a schematic diagram showing a configuration of an X-ray imaging apparatus according to a first embodiment of the present invention.

As shown in FIG. 1, the X-ray imaging apparatus 100 is an apparatus for capturing an X-ray image of a subject S. The X-ray imaging apparatus 100 according to the first embodiment is used for medical applications. In this instance, the subject S is a living body to be examined.

As shown in FIG. 1, the X-ray imaging apparatus 100 is provided with an X-ray source 11, a detector 12, a C-shaped arm 13, a hose 20, a shape retention member 50 (see FIG. 3), a base 30, and an image processing unit 42. The base 30 includes a C-shaped arm support portion 31, a hose attachment portion 60, a biasing unit 33 (see FIG. 4), a cover 34, a first C-shaped arm drive mechanism 35, a second C-shaped arm drive mechanism 36, and a base moving mechanism 37.

The X-ray source 11 is configured to generate X-rays when a high voltage is applied thereto. The X-ray source 11 is configured to emit the generated X-rays toward the detector 12.

The detector 12 is configured to detect the X-rays emitted from the X-ray source 11. The detector 12 is configured to convert the detected X-rays into an electric signal. With this, an X-ray image reflecting the transmission of X-rays in the subject S is obtained. The detector 12 is, for example, an FPD (Flat Panel Detector). The detector 12 is configured by a plurality of conversion elements (not shown) and a plurality of pixel electrodes (not shown) arranged on the plurality of conversion elements. The plurality of conversion elements and pixel electrodes are arranged in a matrix in the detection surface at given periods (pixel pitches). The detection signal (image signal) of the detector 12 is sent to the image processing unit 42.

The C-shaped arm 13 has an arc-shaped configuration. The C-shaped arm 13 supports the X-ray source 11 at one end and the detector 12 at the other end. The C-shaped arm 13 is supported by the C-shaped arm support portion 31 so as to be rotatable in the circumferential direction of the C-shaped arm 13 (in the arrow A direction). The C-shaped arm 13 is supported by the C-shaped arm support portion 31 so as to be rotatable about the axial line of the rotation axis 90.

Figure 2:
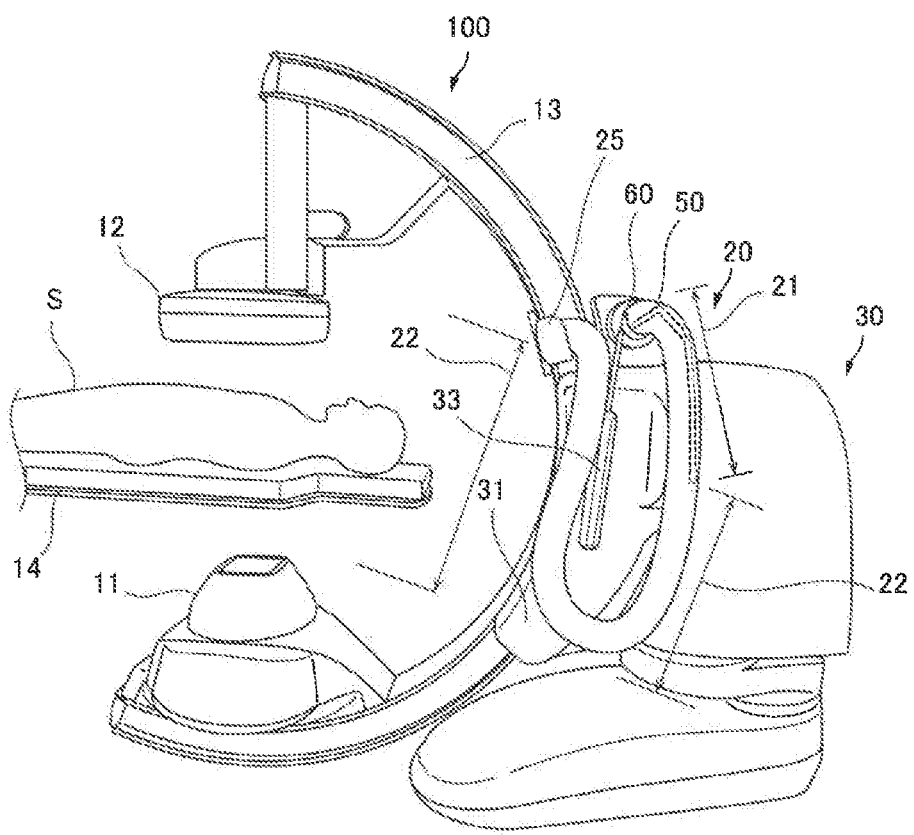
FIG. 2 is a diagram showing one example of a position of a C-shaped arm and a state of a hose.

The hose 20 accommodates therein the wiring 80 connected to at least one of the X-ray source 11 and the detector 12. As shown in FIG. 2, the hose 20 includes a base side portion 21 and an opposite side portion 22 on the opposite side of the base side portion 21.

One end of the base side portion 21 of the hose 20 is attached to the hose attachment portion 60 provided on the base 30. The one end of the base side portion 21 of the hose 20 is held by being fitted into the hose attachment portion 60 (see FIG. 6). One end of the opposite side portion 22 of the hose 20 is connected to the C-shaped arm 13. In the hose 20, the base side portion 21 and the opposite side portion 22 of the hose 20 are one part of the single hose 20 and another part other than the one part, respectively. The hose 20 may include other portions between the base side portion 21 of the hose 20 and the opposite side portion 22 of the hose 20. The hose 20 is made of, for example, resin.

The base side portion 21 of the hose 20 is configured to be less deformable than the opposite side portion 22 of the hose 20. The base side portion 21 of the hose 20 denotes a portion from the root of the hose 20 attached to the hose attachment portion 60 to a predetermined position. The base side portion 21 is a portion in which the shape is held by being contacted by the shape retention member 50 inserted in the hose 20. The opposite side portion 22 of the hose 20 is a portion from a predetermined position to a connection portion 25 connected to the C-shaped arm 13. The shape of the opposite side portion 22 of the hose 20 is configured to be deformable.

Figure 3:
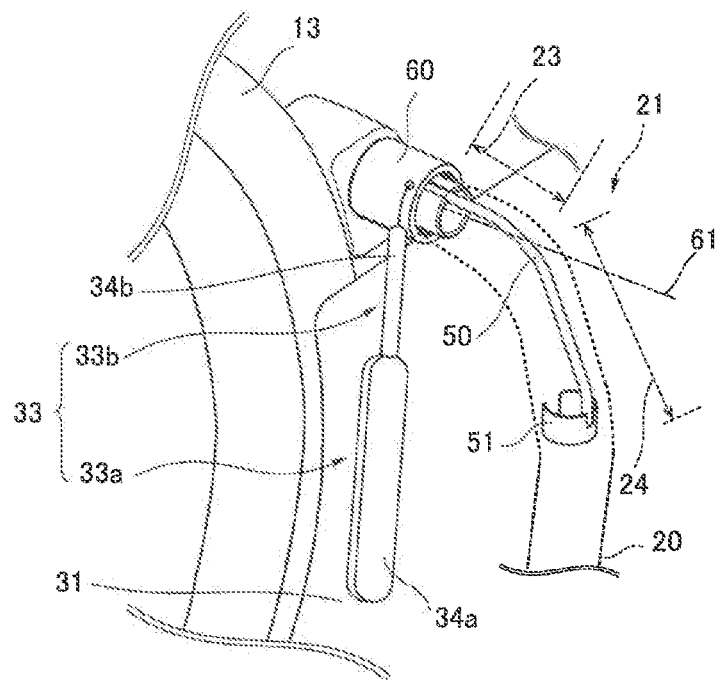
FIG. 3 is a partial perspective view of the X-ray imaging apparatus according to the first embodiment.

As shown in FIG. 3, the base side portion 21 of the hose 20 includes a first portion 23 and a second portion 24. FIG. 3 illustrates the hose 20 with dashed lines and omits the wiring 80 for ease of explanation. The first portion 23 is formed to extend from the hose attachment portion 60 along the central axis 61 of the hose attachment portion 60. The second portion 24 is provided on the opposite side of the first portion 23 opposite to the hose attachment portion 60 and is formed to extend obliquely with respect to the central axis 61 of the hose attachment portion 60. The base side portion 21 of the hose 20 is held in shape by a shape retention member 50.

The shape retention member 50 is configured to retain the shape of the base side portion 21 of the hose 20 by being inserted in the base side portion 21 of the hose 20. The shape retention member 50 is formed such that the root of the shape retention member 50 is connected to the hose attachment portion 60, and the tip end extends to a predetermined position of the hose 20. That is, the shape retention member 50 is formed in a part of the hose 20 attached to the hose attachment portion 60 from the root to a predetermined position.

The shape retention member 50 is formed to extend from the hose attachment portion 60 along the central axis 61 of the hose attachment portion 60 and is formed to extend obliquely with respect to the central axis 61 of the hose attachment portion 60 on the tip end side. The shape retention member 50 is formed of a metal rod-shaped member. At the tip of the shape retention member 50, a holder 51 is provided for bringing together the wiring 80 and guiding the wiring 80.

Figure 4:
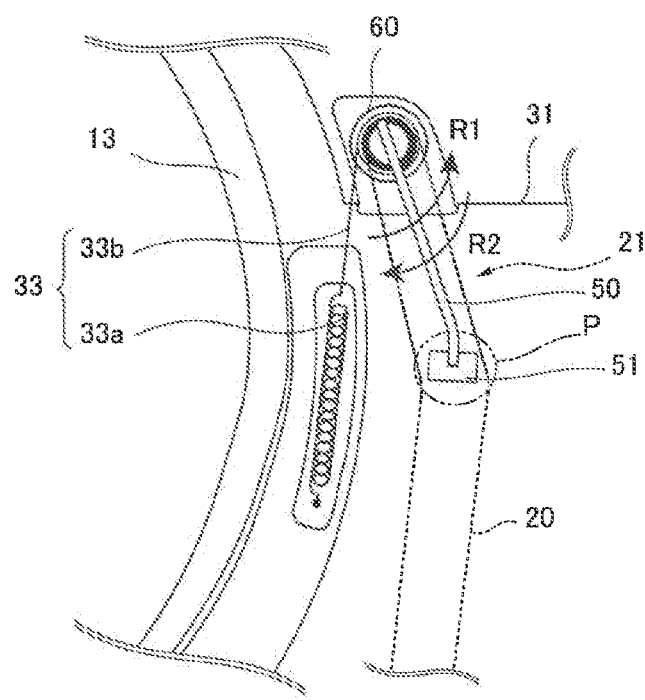
FIG. 4 is a partial side view of the X-ray imaging apparatus according to the first embodiment.

As shown in FIG. 4, the shape retention member 50 is configured such that the root of the shape retention member 50 is rotated in the first rotation direction R1 by the biasing unit 33 so that the tip end side is rotated in the first rotation direction R1 together with the base side portion 21 of the hose 20. The rotation of the base side portion 21 of the hose 20 by the biasing unit 33 in the first rotation direction R1 will be described later.

As shown in FIG. 1, the C-shaped arm support portion 31 is provided on the C-shaped arm side of the base 30. The C-shaped arm support portion 31 supports the C-shaped arm 13 by sandwiching the arm in a direction perpendicular to the circumferential direction of the C-shaped arm 13 (see FIG. 2). The C-shaped arm support portion 31 rotatably supports the C-shaped arm 13 in the circumferential direction (in the arrow A direction) of the C-shaped arm 13 by a first C-shaped arm drive mechanism 35. Further, the C-shaped arm support portion 31 supports the C-shaped arm 13 by the second C-shaped arm drive mechanism 36 so as to be rotatable about the axial line of the rotation axis 90.

As shown in FIG. 2, the hose attachment portion 60 is provided at the upper portion of the C-shaped arm support portion 31. One end of the base side portion 21 of the hose 20 is rotatably attached to the hose attachment portion 60. That is, the root of the hose 20 is rotatably attached to the hose attachment portion 60.

Figure 5:
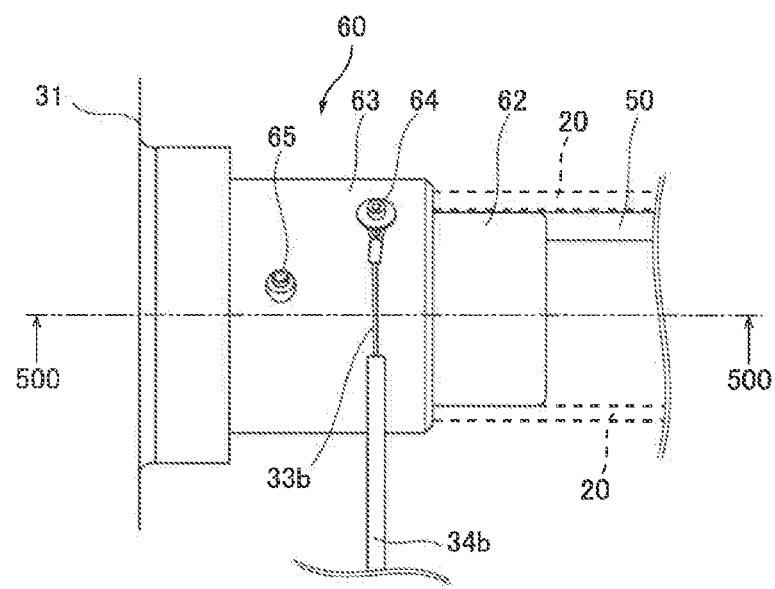
FIG. 5 is a side view of a hose attachment portion.

As shown in FIG. 5, the hose attachment portion 60 includes an inner cylindrical portion 62 and an outer cylindrical portion 63 on the outer peripheral side of the inner cylindrical portion 62. The outer periphery of the hose attachment portion 60 is covered with a cover (not shown) for the hose attachment portion. One end of the hose 20 is attached by being fitted between the inner cylindrical portion 62 and the outer cylindrical portion 63. The root of the shape retention member 50 is connected to the inner cylindrical portion 62 of the hose attachment portion 60. To the wire connection portion 64 on the outer peripheral surface of the outer cylindrical portion 63 of the hose attachment portion 60, one end of the wire 33b of the biasing unit 33 is attached. The inner cylindrical portion 62 and the outer cylindrical portion 63 are fixed by screw fastening with a screw 65.

Figure 6:
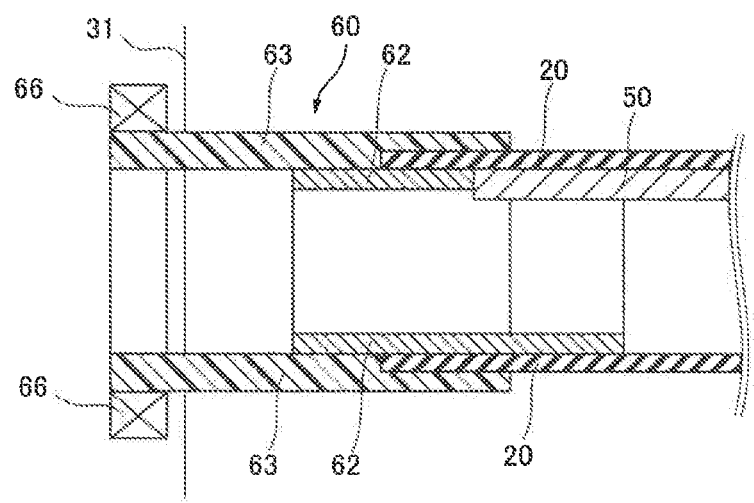
FIG. 6 is a cross-sectional schematic diagram taken along the line 500-500 in FIG. 5.

As shown in FIG. 6, the outer cylindrical portion 63 of the hose attachment portion 60 is rotatably connected to the bearing 66 provided to the C-shaped arm support portion 31. With this configuration, the hose attachment portion 60 including the inner cylindrical portion 62 and the outer cylindrical portion 63 is configured to be rotatable about the central axis 61 (see FIG. 3) of the hose attachment portion 60 with respect to the C-shaped arm support portion 31 together with the shape retention member 50 and the base side portion 21 of the hose 20.

As shown in FIG. 4, the biasing unit 33 is provided on the side surface of the C-shaped arm support portion 31. FIG. 4 omits the illustration of the cover 34 for ease of explanation. The biasing unit 33 is configured to bias the base side portion 21 of the hose 20 to rotate about the central axis 61 (see FIG. 3) of the hose attachment portion 60 in the first rotation direction R1 away from the C-shaped arm 13 outward. The biasing unit 33 includes a tension spring 33a and a wire 33b connected to the tension spring 33a.

One end of the wire 33b is connected to the wire connection portion 64 of the outer cylindrical portion 63 of the hose attachment portion 60 (see FIG. 5). The other end of the wire 33b is connected to the one end of the tension spring 33a. One end of the tension spring 33a is connected to the other end of the wire 33b. The other end of the tension spring 33a is connected to the C-shaped arm support portion 31. The tension spring 33a is configured to bias the base side portion 21 of the hose 20 to rotate in the first rotation direction R1 by rotating the hose attachment portion 60 via the wire 33b.

As shown in FIG. 2, the biasing unit 33 is disposed between the C-shaped arm support portion 31 and the hose 20. With this configuration, the biasing unit 33 is disposed so as to be surrounded by the C-shaped arm support portion 31 and the hose 20 extending from the hose attachment portion 60. As a result, it is possible to prevent the biasing unit 33 including the cover 34 from coming into contact with the subject S placed on the top board 14 or the user in the vicinity of the X-ray imaging apparatus 100.

As shown in FIG. 3, the cover 34 is configured to cover the biasing unit 33. The cover 34 includes a tension spring cover 34a provided on the C-shaped arm support portion 31 to cover the tension spring 33a and a wire cover 34b covering the outer periphery of the wire 33b.

The tension spring 33a of the biasing unit 33 is provided on the side surface of the C-shaped arm support portion 31 and extends along the side surface of the C-shaped arm support portion 31. The wire 33b of the biasing unit 33 is exposed by a short distance from the upper end of the tension spring cover 34a to the hose attachment portion 60 and extends along the side surface of the C-shaped arm support portion 31. Note that the portion of the wire 33b exposed from the tension spring cover 34a is covered with a wire cover 34b.

As shown in FIG. 1, the first C-shaped arm drive mechanism 35 is configured to drive the C-shaped arm 13. The first C-shaped arm drive mechanism 35 is provided inside the C-shaped arm support portion 31. The first C-shaped arm drive mechanism 35 is configured to include a motor and an actuator.

The second C-shaped arm drive mechanism 36 is configured to drive the C-shaped arm support portion 31. The second C-shaped arm drive mechanism 36 is provided inside the C-shaped arm support portion 31. The second C-shaped arm drive mechanism 36 is composed of a motor and an actuator.

The base moving mechanism 37 is configured to move the base 30 installed on the floor to move the C-shaped arm 13 together with the base 30 to a desired imaging position. The base moving mechanism 37 is provided inside the base 30. The base moving mechanism 37 is configured to include a motor and an actuator.

The image processing unit 42 is provided in the controller 40. The controller 40 is configured by, for example, a PC (personal computer). The controller 40 is provided with a control unit 41, an image processing unit 42, and a storage unit 43.

The control unit 41 is configured by a processor, such as, e.g., a CPU (Central Processing Unit) and controls imaging in the X-ray imaging apparatus 100 by executing an application program stored in the storage unit 43. Further, the control unit 41 performs control for placing the C-shaped arm 13 and the base 30 at predetermined positions by the first C-shaped arm drive mechanism 35, the second C-shaped arm drive mechanism 36, and the base moving mechanism 37.

The image processing unit 42 generates an image based on a detection signal output from the detector 12. The image processing unit 42 is configured by a processor, such as, e.g., a GPU (Graphics Processing Unit) and an FPGA (Field-Programmable Gate Array configured for image processing.

The storage unit 43 is configured to include a volatile storage unit and a non-volatile storage unit. The storage unit 43 stores a program or the like. The storage unit 43 stores an image generated by the image processing unit 42.

(Rotation of Base Side Portion of Hose by Biasing Unit)

With reference to FIG. 4, the rotation of the base side portion 21 of the hose 20 by the biasing unit 33 in the first rotation direction R1 will be described. FIG. 4 is a partial side view showing the vicinity of the biasing unit 33 at the position of the C-shaped arm 13 and the state of the hose 20 in FIG. 2.

In the state shown in FIG. 4, in the vicinity of the bearing 66 provided to the C-shaped arm support portion 31, a convex member (not shown) provided inside the C-shaped arm support portion 31 and fixed thereto and a rotatable contact member (not shown) provided to the hose attachment portion 60 and configured to be brought into contact with the convex member are provided. Since the convex member abuts against the abutment member, it is restricted that the hose attachment portion 60 rotates in the first rotation direction R1 more than indicated by FIG. 4. That is, the opposite side of base side portion of the hose 20 opposite to the hose attachment portion 60 is disposed at an outside limit position P outwardly away from the C-shaped arm 13 than the hose attachment portion 60.

Figure 7:
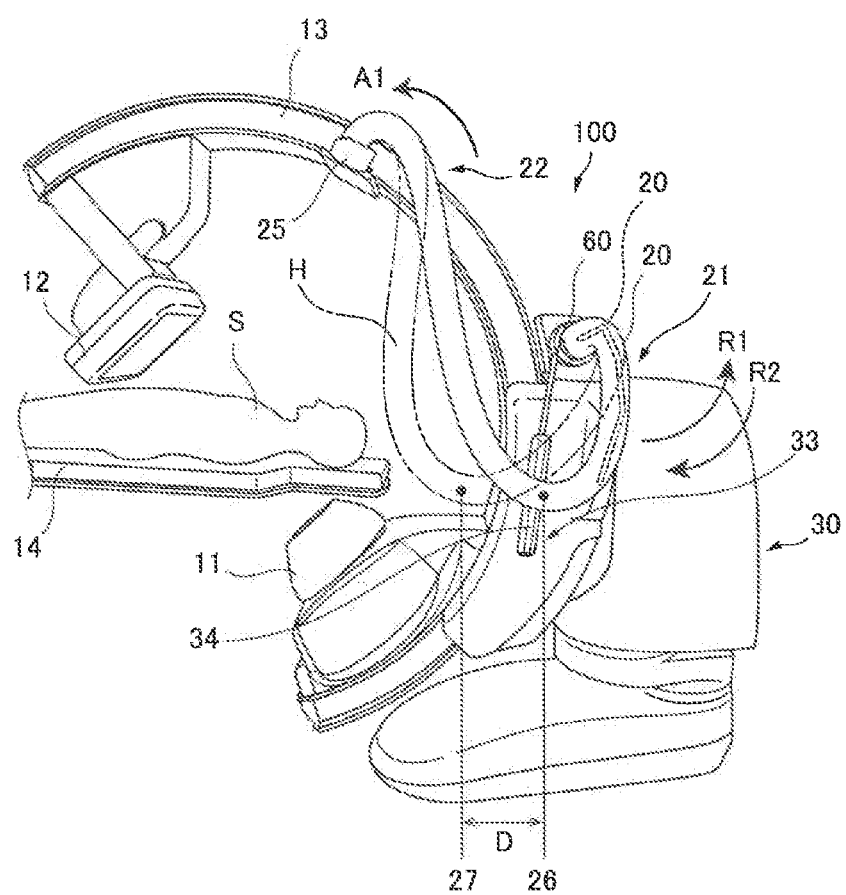
FIG. 7 is a diagram showing another example of the position of the C-shaped arm and the state of the hose.

Here, when the C-shaped arm 13 is moved in the circumferential direction (in the A1 direction in FIG. 1) so that the detector 12 moves from the head side of the subject S toward the foot side from the state shown in FIG. 7 to the state shown in FIG. 7, the connection portion 25 of the opposite side portion 22 of the hose 20 connected to the C-shaped arm 13 moves from the head side of the subject S toward the foot side along the circumferential direction of the C-shaped arm 13. Due to the movement of the connection portion 25 of the hose 20 connected to the C-shaped arm 13 in the A1 direction, a pulling force toward the inner side of the C-shaped arm 13 is generated at the base side portion 21 of the hose 20.

However, a force for rotating the base side portion 21 of the hose 20 in a second rotation direction R2 opposite to the first rotation direction R1 is generated, while the tension spring 33a applies a biasing force for rotating the base side portion 21 of the hose 20 in the first rotation direction R1 outwardly away from the C-shaped arm 13. As a result, it is possible to suppress the rotation of the base side portion 21 of the hose 20 in the second rotation direction R2 opposite to the first rotation direction R1 due to the movement of the hose 20 toward the inside of the C-arm on the opposite side.

Figure 8:
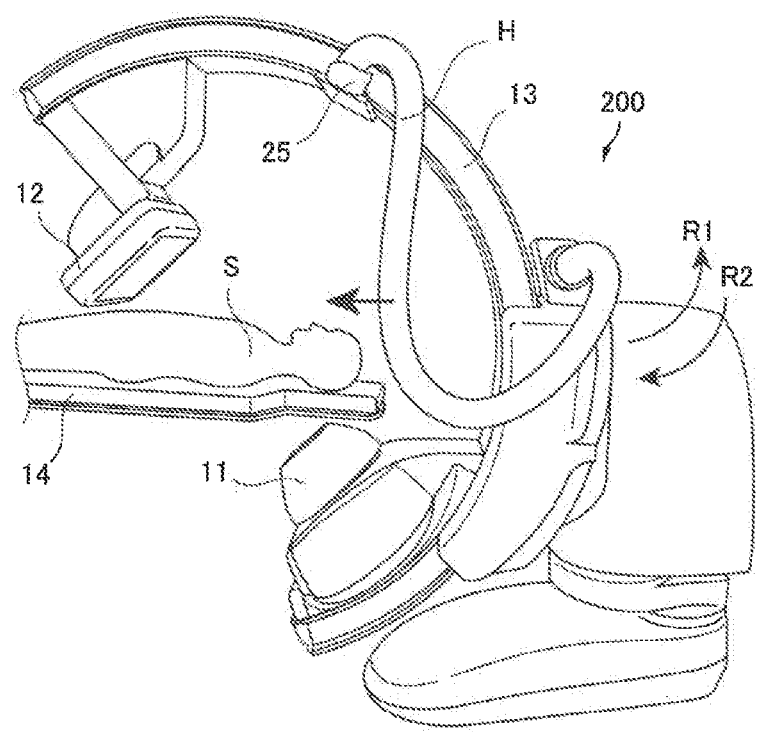
FIG. 8 is a diagram showing the state of the hose at the position of the C-shaped arm shown in FIG. 7 according to Comparative Example.

On the other hand, in the X-ray imaging apparatus 200 according to Comparative Example shown in FIG. 8, since the biasing unit 33 is not provided, the biasing force for rotating the base side portion of the hose H in the first rotation direction R1 away from the C-shaped arm 13 is not applied. Further, since the hose H is flexible and the shape retention member 50 is not provided, the shape of the base side portion of the hose H is not retained.

For this reason, it is not possible to suppress the rotation of the base side portion of the hose H in the second rotation direction R2 opposite to the first rotation direction R1 due to the movement of the C-shaped arm 13 toward the inner side on the opposite side of the hose H. Therefore, there is a possibility that the hose H approaches the subject S placed on the top board 14 by the inward pulling force of the C-shaped arm 13 against the base side portion of the hose H due to the inward movement of the C-shaped arm 13 on the opposite side of the hose H. Consequently, there is a possibility that the hose H comes into contact with the subject S.

The hose 20 is flexible, and therefore, the intermediate portion of the hose 20 naturally sags downward due to the action of the gravitational force. If the root of the hose 20 on the hose attachment portion side is simply rotated, the hose 20 is merely twisted.

However, as shown in FIG. 7, the base side portion 21 of the hose 20 according to the first embodiment is configured to be hard to deform. Therefore, a biasing force that attempts to remain at a position away from the subject S acts on a predetermined position corresponding to the tip end of the shape retention member 50. Consequently, when the connection portion 25 of the hose 20 is moved toward the subject S in accordance with the circumference directional movement of the C-shaped arm 13, the position of the most hanging portion 26 in the middle of the hose 20 becomes a position away from the subject S by the distance D from the position of the most hanging portion 27 when the hose 20 hangs naturally (shown by a two-dot chain line).

Effects of First Embodiment

In the first embodiment, the following effects can be obtained.

In the first embodiment, as described above, the X-ray imaging apparatus 100 is provided with the X-ray source 11, the detector 12 for detecting X-rays emitted from the X-ray source 11, the C-shaped arm 13 for supporting the X-ray source 11 and the detector 12, the hose 20 for accommodating the wiring 80 connected to at least one of the X-ray source 11 and the detector 12, the hose 20 including the base side portion 21 and the opposite side portion 22 connected to the C-shaped arm on the opposite side of the base side portion 21, the base 30 including the C-shaped arm support portion 31 for rotatably supporting the C-shaped arm 13 and the hose attachment portion 60 to which the base side portion 21 of the hose 20 is rotatably connected, the biasing unit 33 for biasing the base side portion 21 of the hose 20 to rotate in the first rotation direction R1 outwardly away from the C-shaped arm 13 about the hose attachment portion 60, and the image processing unit 42 for generating the image based on the detection signal output from the detector 12.

With this configuration, even in a case where the position of the opposite side portion 22 of the hose 20 connected to the C-shaped arm 13 is changed in accordance with the movement of the C-shaped arm at least in the circumference direction, it is possible to suppress the distance between the hose 20 and the subject S placed on the top board 14 from decreasing since the base side portion 21 of the hose 20 is biased by the biasing unit 33 to rotate in the first rotation direction R1 outwardly away from the C-shaped arm 13. Therefore, it is possible to prevent the hose 20 from coming into contact with the subject S placed on the top board 14 in accordance with the movement of the C-shaped arm 13 at least in the circumferential direction.

Further, in the first embodiment, as described above, the base side portion 21 of the hose 20 is formed to extend from the hose attachment portion 60 along the central axis 61 of the hose attachment portion 60 and is formed to obliquely extend with respect to the central axis 61 of the hose attachment portion 60 at the opposite side of the hose attachment portion 60, and the biasing unit 33 urges the base side portion 21 of the hose 20 about the central axis 61 of the hose attachment portion 60 in the first rotation direction R1.

Thus, the biasing unit 33 urges the base side portion 21 of the hose 20 to rotate about the central axis 61 of the hose attachment portion 60 in the first rotation direction R1, and therefore, the opposite side of the base side portion 21 of the hose 20 opposite to the hose attachment portion 60 is biased to rotate in the first rotation direction R1 outwardly away from the C-shaped arm 13. Therefore, it is possible to prevent the opposite side of the hose attachment portion 60 opposite to the base side portion 21 of the hose 20 from approaching the subject S placed on the top board 14. Therefore, it is possible to further suppress the hose 20 from coming into contact with the subject S placed on the top board 14.

Further, in the first embodiment, as described above, the opposite side of the base side portion 21 of the hose 20 is arranged at the outside limit position P outwardly away from the C-shaped arm 13 than the hose attachment portion 60, and the biasing unit 33 urges the base side portion 21 of the hose 20 to suppress the rotation of the base side portion 21 in the second rotation direction R2 opposite to the first rotation direction R1 in accordance with the inner movement of the C-shaped arm 13 on the opposite side of the hose 20.

With this configuration, the opposite side of the base side portion 21 of the hose 20 opposite to the hose attachment portion 60 is arranged at the outside limit position P, and therefore, the opposite side portion 22 of the hose 20 can maintain a satisfactory distance to the subject S placed on the top board 14. Therefore, it is possible to more appropriately suppress the hose 20 from coming into contact with the subject S placed on the top board 14 in accordance with the movement of the C-shaped arm C 13 at least in the circumferential direction.

Further, in the first embodiment, as described above, the base side portion 21 of the hose 20 is configured not to be easily deformed. Thus, even when the position of the opposite side portion 22 of the hose 20 connected to the C-shaped arm 13 is changed in accordance with the movement of the C-shaped arm 13 at least in the circumferential direction, it is possible to suppress the distance between the hose 20 and the subject S placed on the top board 14 from decreasing due to the shape change in the base side portion 21 of the hose 20 since the base side portion 21 of the hose 20 is formed to be hard to deform.

In addition, in first embodiment, as described above, the shape retention member 50 is further provided. The root of the shape retention member 50 is connected to the hose attachment portion 60. The shape retention member 50 extends the inside of the base side portion 21 to maintain the shape of the base side portion 21 of the hose, and the root of the shape retention member 50 is rotated by the biasing unit 33, so that the tip end side of the shape retention member 50 is rotated in the first rotation direction R1 together with the base side portion 21 of the hose 20. With this configuration, the shape retention member 50 can hold the shape of the base side portion 21 of the hose 20 so as not to be deformed, and therefore, it is possible to appropriately suppress the decrease in the distance between the hose 20 and the subject S placed on the top board 14 due to the shape change of the base side portion 21 of the hose 20.

Further, in the first embodiment, as described above, the shape retention member 50 is formed to extend from the hose attachment portion 60 along the central axis 61 of the hose attachment portion 60 and is formed to extend obliquely with respect to the central axis 61 of the hose attachment portion 60 at the tip end side.

With this configuration, the root of the shape retention member 50 is biased to rotate in the first rotation direction R1 about the central axis 61 of the hose attachment portion 60 by the biasing force of the biasing unit 33, and therefore, the opposite side of the base side portion 21 of the hose 20 opposite to the hose attachment portion 60 is biased to assuredly rotate in the first rotation direction R1 outwardly away from the C-shaped arm 13. Therefore, it is possible to suppress the opposite side of the base side portion 21 of the hose 20 opposite to the hose attachment portion 60 from approaching the subject S placed on the top board 14. Therefore, it is possible to suppress the hose 20 from coming into contact with the subject S placed on the top board 14.

Further, in the first embodiment, as described above, the shape retention member 50 is made of a metal rod-shaped member. Thus, even in a case where the position of the opposite side portion 22 on the opposite side of the base side portion 21 of the hose 20 connected to the C-shaped arm 13 is changed, it is possible to assuredly hold the shape of the base side portion 21 of the hose 20 by the hardly deformable metal rod-shaped member.

Further, in the first embodiment, as described above, the biasing unit 33 is provided on the base 30. Accordingly, even in a case where the C-shaped arm 13 is moved in the circumferential direction, the positional relation between the biasing unit 33 and the hose attachment portion 60 attached to the base 30 does not change. Therefore, the biasing unit 33 can bias the base side portion 21 of the hose 20 in the first rotation direction R1 about the central axis 61 of the hose attachment unit 60 without being affected by the circumferential movements of the C-shaped arm 13.

Further, in the first embodiment, as described above, the cover 34 is further provided. The cover 34 is provided on the base 30 to cover the biasing unit 33, as described above. Accordingly, it is possible to appropriately prevent the wire 33b and the tension spring 33a constituting the biasing unit 33 from directly coming into contact with the subject S mounted on the top board 14.

Further, in the first embodiment, as described above, the biasing unit 33 includes the tension spring 33a and the wire 33b with one end connected to the tension spring 33a and the other end connected to the hose attachment portion 60. The tension spring 33a can bias the base side portion 21 of the hose 20 to rotate in the first rotation direction R1 and can position the wire 33b along the outer surface of the hose attachment portion 60. Therefore, unlike the case in which the biasing unit 33 is configured by only the tension spring 33a, it is possible to appropriately connect the wire 33b to the hose attachment portion 60.

Further, in the first embodiment, as described above, the tension spring 33a biases the base side portion 21 of the hose 20 to rotate in the first rotation direction R1 by rotating the hose attachment portion 60 via the wire 33b. Accordingly, the base side portion 21 of the hose 20 can be biased to be assuredly rotated in the first rotation direction R1, and therefore, it is possible to more appropriately suppress the decrease in the distance between the hose 20 and the subject S placed on the top board 14 due to the shape change of the base side portion 21 of the hose 20.

Further, in the first embodiment, the C-shaped arm 13 is configured to be a floor-mounted C-shaped arm supported by a base 30 mounted on a floor of an examination room or an overhead traveling C-shaped arm supported by a base mounted on a ceiling of an examination room. Accordingly, even in a case where the X-ray imaging apparatus 100 is provided with either the floor-mounted C-shaped arm 13 or the overhead traveling C-shaped arm, it is possible to suppress the hose 20 from coming into contact with the subject S placed on the top board 14 in accordance with the movement of the C-shaped arm 13 at least in the circumferential direction.

Second Embodiment (Configuration of X-Ray Imaging Apparatus)

Figure 9:
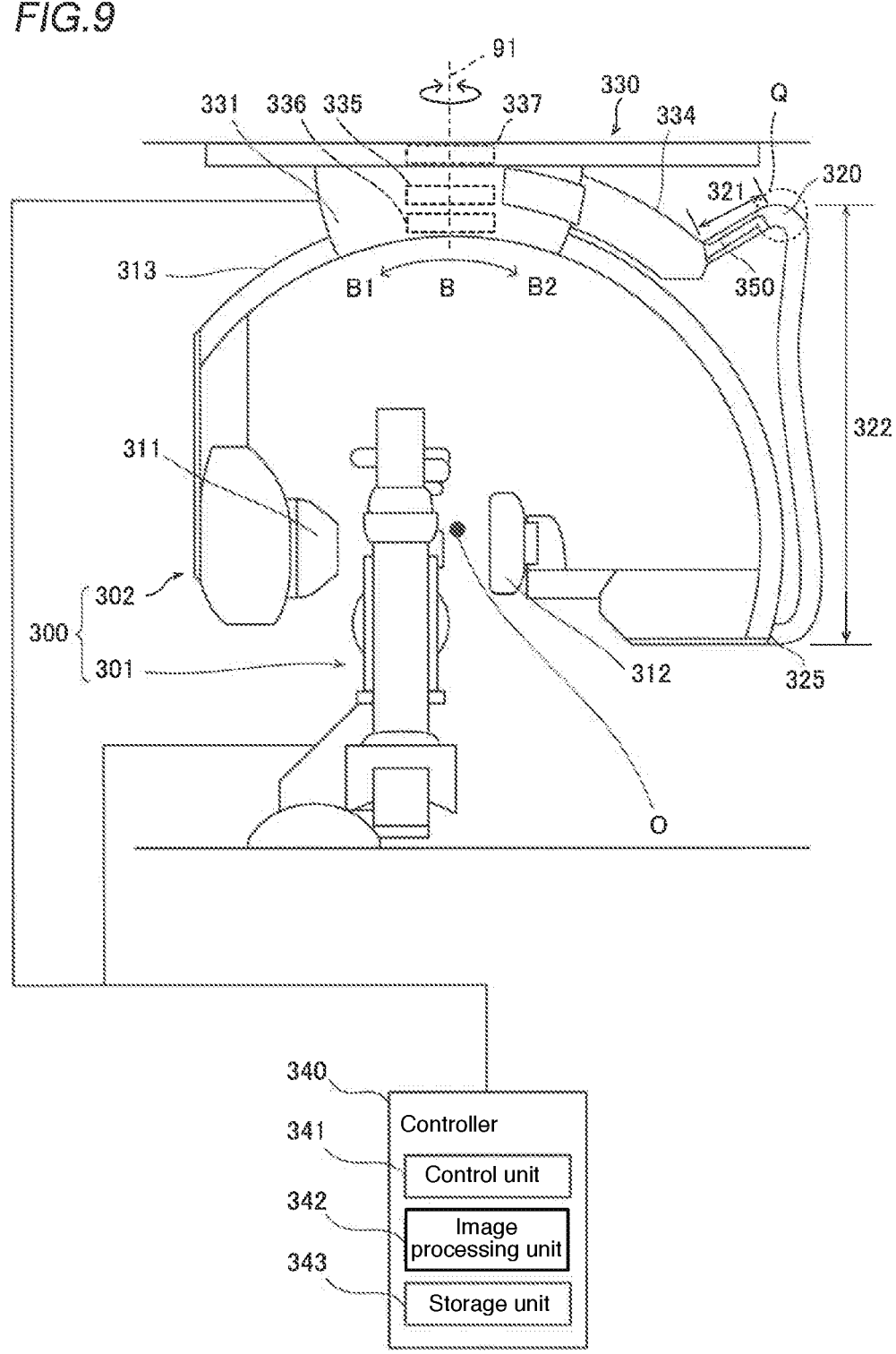
FIG. 9 is a schematic diagram showing a configuration of an X-ray imaging apparatus according to a second embodiment of the present invention.

Next, with reference to FIG. 9 to FIG. 15, the configuration of an X-ray imaging apparatus 300 according to a second embodiment will be described. In the second embodiment, unlike the first embodiment which is a single-plane type X-ray imaging apparatus 100 provided with one floor-mounted C-shaped arm 13, the X-ray imaging apparatus 300 is a biplane type X-ray imaging apparatus 300 provided with both a floor-mounted C-shaped arm 13a and an overhead traveling C-shaped arm 313, as shown in FIG. 9. Note that the same reference symbol is allotted to the same configuration as that of the first embodiment, and the description thereof will be omitted.

Figure 10:
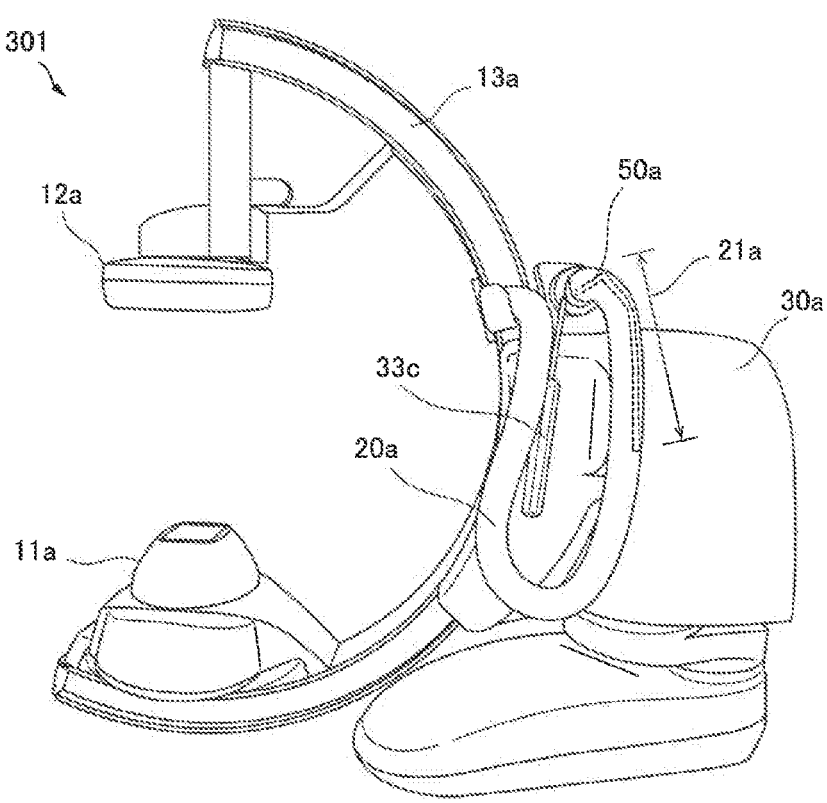
FIG. 10 is a schematic diagram showing one example of a floor-mounted X-ray imaging unit according to the second embodiment.

As shown in FIG. 9, the X-ray imaging apparatus 300 is provided with a floor-mounted X-ray imaging unit 301, a ceiling-mounted X-ray imaging unit 302, and an image processing unit 342. As shown in FIG. 10, the floor-mounted X-ray imaging unit 301 includes a first X-ray source 11a, a first detector 12a, a floor-mounted C-shaped arm 13a, a first hose 20a, a first shape retention member 50a, a first base 30a, and a first biasing unit 33c, which are the same as the X-ray source 11, the detector 12, the C-shaped arm 13, the hose 20, the shape retention member 50, the base 30, and the biasing unit 33, respectively, of the X-ray imaging apparatus 100 (see FIG. 2), of the above-described first embodiment.

Note that the explanations of the first X-ray source 11a, the first detector 12a, the floor-mounted C-shaped arm 13a, the first hose 20a, the first shape retention member 50a, the first base 30a, and the first biasing unit 33c in the floor-mounted X-ray imaging unit 301 will be omitted.

Figure 13:
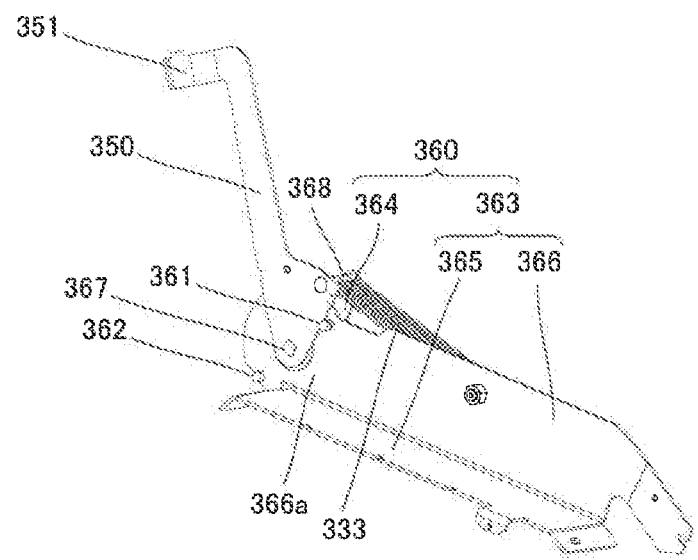
FIG. 13 is Example 1 of a partial perspective view of the X-ray imaging apparatus according to the second embodiment.

The ceiling-mounted X-ray imaging unit 302 includes a second X-ray source 311, a second detector 312, an overhead traveling C-shaped arm 313, a second hose 320, a second shape retention member 350, a second base 330, a second biasing unit 333 (see FIG. 11), a first stopper 361 (see FIG. 13), and a second stopper 362 (see FIG. 13).

The second base 330 includes an overhead traveling C-shaped arm support portion 331, a second hose attachment portion 360 (see FIG. 11), a second cover 334, a third C-shaped arm driving mechanism 335, a fourth C-shaped arm driving mechanism 336, and a second base moving mechanism 337.

The second X-ray source 311 and the second detector 312 of the ceiling-mounted X-ray imaging unit 302 are the same as those of the X-ray source 11 and the detector 12 in the first embodiment, respectively, and therefore, the explanation thereof will be omitted. Note that in FIG. 11, the second cover 334 is not illustrated for convenience of explanation.

The overhead traveling C-shaped arm 313 has an arcuate shape. The overhead traveling C-shaped arm 313 supports the second X-ray source 311 at one end and the second detector 312 at the other end. The overhead traveling C-shaped arm 313 is rotatably supported by the overhead traveling C-shaped arm support portion 331 in the circumferential direction of the overhead traveling C-shaped arm 313 (see the arrow B direction). The overhead traveling C-shaped arm 313 is supported by the overhead traveling C-shaped arm support portion 331 to be rotatable about the axial line of the rotation axis 91. Further, the overhead traveling C-shaped arm 313 is supported by the overhead traveling C-shaped arm support portion 331 to be movable in the direction (direction in front and back of the paper surface of FIG. 9) along the rotation center line O.

The second hose 320 accommodates therein wiring (not shown) connected to at least one of the second X-ray source 311 and the second detector 312. The second hose 320 includes a base side portion 321, an opposite side portion 322 opposite to the base side portion 321. One end of the base side portion 321 of the second hose 320 is attached to the second hose attachment portion 360 (see FIG. 12) provided on the second base 330.

The base side portion 321 of the second hose 320 is configured to include an end attached to the second hose attachment portion 360. The other end of the opposite side portion 322 of the second hose 320 is connected to the overhead traveling C-shaped arm 313. The opposite side portion 322 of the second hose 320 is configured to include an end connected to the overhead traveling C-shaped arm 313. The base side portion 321 of the second hose 320 and the opposite side portion 322 of the second hose 320 are one part in a single hose and the other part other than the one part, respectively.

The second hose 320 may include other portions between the base side portion 321 of the second hose 320 and the opposite side portion 322 of the second hose 320. The second hose 320 is made of, for example, resin.

The base side portion 321 of the second hose 320 is a portion ranging from the root of the second hose 320 attached to the second hose attachment portion 360 to a predetermined position. The predetermined position is a position where the outer peripheral surface of the second hose 320 is supported by the second shape retention member 350. The opposite side portion 322 of the second hose 320 denotes a part from the predetermined position to the connection portion 325 connected to the overhead traveling C-shaped arm 313.

Figure 11:
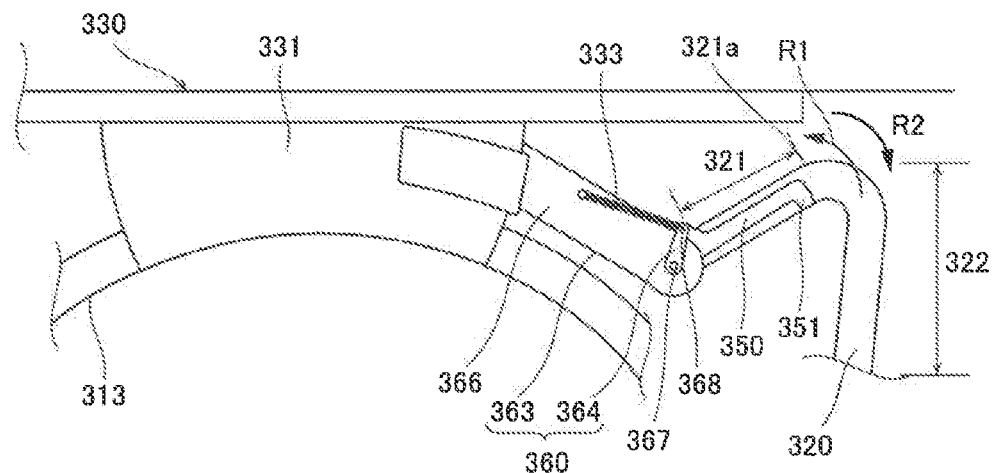
FIG. 11 is a schematic diagram showing a ceiling-mounted X-ray imaging unit according to a second embodiment.

As shown in FIG. 11, the second shape retention member 350 is formed such that one end of the second shape retention member 350 is rotatably connected to the second hose attachment portion 360, and the other end extends to the predetermined position of the second hose 320. One end of the second shape retention member 350 is attached to the member second portion 366 of the second hose attachment portion 360. The second shape retention member 350 is configured to retain the shape of the base side portion 321 of the second hose 320. At the other end of the second shape retention member 350, a holder 351 (see FIG. 13) for supporting the outer peripheral surface of the second hose 320 is provided. The second shape retention member 350 is configured to support the second hose 320 from below by the holder 351. The second shape retention member 350 is formed of a metal plate-like member.

The second shape retention member 350 is configured such that the other end side of the second shape retention member 350 is rotated in the first rotation direction R1 about the same rotation shaft 367 as the rotation member 364 together with the base side portion 321 of the second hose 320. The second shape retention member 350 is rotatably connected to the second hose attachment portion 360. The second shape retention member 350 is rotatably supported by the rotation shaft 367 (see FIG. 13). The rotation of the base side portion 321 of the second hose 320 in the first rotation direction R1 of the base side portion 321 by the second biasing unit 333 will be described later.

The overhead traveling C-shaped arm support portion 331 is mounted on the ceiling of the examination room. The overhead traveling C-shaped arm support portion 331 supports the overhead traveling C-shaped arm 313 by sandwiching it in the direction perpendicular to the circumferential direction.

Figure 12:
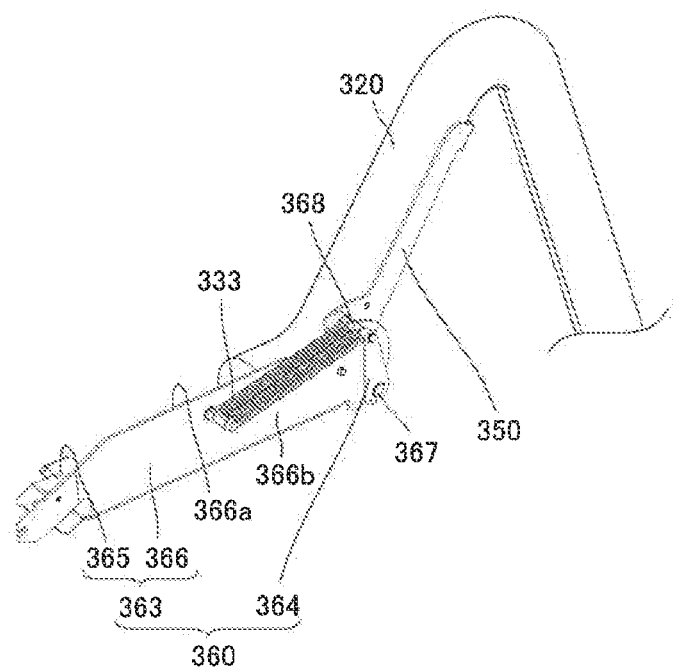
FIG. 12 is a partial side view of the X-ray imaging apparatus according to the second embodiment.

As shown in FIG. 12, the second hose attachment portion 360 is provided to protrude from the side surface of the overhead traveling C-shaped arm support portion 331. The second hose attachment portion 360 includes a root mounting member 363 and a rotation member 364.

As shown in FIG. 13, the root mounting member 363 is an L-shaped plate-like member. The root mounting member 363 includes a member first portion 365 and a member second portion 366. One end of the member first portion 365 extending in the longitudinal direction intersects one end of the member second portion 366 extending in the longitudinal direction. The root mounting member 363 is formed of, for example, a metal member. Note that in FIG. 13, the illustration of the second hose 320 is omitted for convenience of explanation.

As shown in FIG. 12, to the member first portion 365 of the root mounting member 363, the root of the second hose 320 is attached. The second shape retention member 350 and the rotation member 364 are connected to the member second portion 366 of the root mounting member 363. The second shape retention member 350 is connected to the surface 366a of the member second portion 366 facing the second hose 320, and the rotation member 364 is connected to the surface 366a of the member second portion 366 opposite to the surface 366b of the member second portion 366.

That is, the second shape retention member 350 is arranged on one side of the member second portion 366 of the root mounting member 363, and the rotation member 364 is arranged on the other side. The second shape retention member 350 and the rotation member 364 are connected via the rotation shaft 367 and the connection member 368. The second shape retention member 350 and the rotation member 364 are rotatably mounted relative to the member second portion 366 of the root mounting member 363.

The rotation member 364 is formed of, for example, a metal plate-like member. The rotation member 364 is configured to be capable of interlocking with the second shape retention member 350 via the rotation shaft 367 and the connection member 368. The rotation member 364 is configured to be rotatable about the rotation shaft 367 with respect to the member second portion 366 of the root mounting member 363 together with the second shape retention member 350 and the base side portion 321 of the second hose 320.

The connection member 368 is configured to couple the end portion of the rotation member 364 on the opposite side of the rotation shaft 367 and one end of the second shape retention member 350. The connection member 368 is provided not to come into contact with the member second portion 366 of the root mounting member 363 when the rotation member 364 and the second shape retention member 350 are rotated. The connection member 368 is, for example, a metal rod-shaped member.

As shown in FIG. 11, the second biasing unit 333 is configured to bias the base side portion 321 of the second hose 320 to upwardly rotate in the first rotation direction R1 about the rotation shaft 367 extending along the rotation center line O (see FIG. 9) of the overhead traveling C-shaped arm 313. Further, the second biasing unit 333 is configured to suppress the base side portion 321 of the second hose 320 to downwardly rotate about the rotation shaft 367 in the second rotation direction R2 opposite to the first rotation direction R1. The second biasing unit 333 is configured by a tension spring. The second biasing unit 333 has one end connected to the member second portion 366 of the root mounting member 363 and the other end connected to the connection member 368.

As shown in FIG. 13, a first stopper 361 is provided on the upper portion of the surface 366a of the member second portion 366 of the root mounting member 363. The first stopper 361 is configured to restrict the base side portion 321 of the second hose 320 to rotate in the first rotation direction R1 (see FIG. 11) upward in a state in which the second hose 320 is positioned at the upper limit position Q (see FIG. 9).

That is, the first stopper 361 is configured to restrict the second shape retention member 350 to rotate in the first rotation direction R1 upward in a state in which the second hose 320 is positioned at the upper limit position Q. As viewed from the direction along the rotation center line O (see FIG. 9) of the overhead traveling C-shaped arm 313, the upper limit position Q is a position where the opposite side 321a (see FIG. 11) of the base side portion 321 of the second hose 320 opposite to the second hose attachment portion 360 is outwardly away from the second hose attachment portion 360 and upwardly away from the second hose attachment portion 360.

The first stopper 361 is configured by, for example, a metal rod-shaped member. In a state in which the second hose 320 is positioned at the upper limit position Q, the first stopper 361 abuts against the second shape retention member 350, and therefore, the rotation of the second shape retention member 350 in the first rotation direction R1 is restricted by the second biasing unit 333. Note that in FIG. 13, the illustration of the second hose 320 is omitted for convenience of explanation.

The second stopper 362 is provided at a lower portion of the surface 366a of the member second portion 366 of the root mounting member 363. The second stopper 362 is configured to restrict the base side portion 321 of the second hose 320 to rotate in the second rotation direction R2 downward beyond a predetermined range. The second stopper 362 does not limit the rotation angle of the overhead traveling C-shaped arm 313 but is configured to restrict the second hose 320 to further downwardly rotate by incorrect downward tension by the subject or the like, for example, when the overhead traveling C-shaped arm 313 moves in the circumferential direction (B2 direction in FIG. 9). The second stopper 362 is configured by, for example, a metal rod-shaped member.

As shown in FIG. 9, the second cover 334 is configured to cover the second hose attachment portion 360 (see FIG. 11), the rotation member 364 (see FIG. 11), and the second biasing unit 333 (see FIG. 11).

The third C-shaped arm driving mechanism 335 is configured to drive the overhead traveling C-shaped arm 313. The third C-shaped arm driving mechanism 335 is provided inside the overhead traveling C-shaped arm support portion 331. The third C-shaped arm driving mechanism 335 includes a motor and an actuator.

The fourth C-shaped arm driving mechanism 336 is configured to drive the overhead traveling C-shaped arm support portion 331. The fourth C-shaped arm driving mechanism 336 is provided inside the overhead traveling C-shaped arm support portion 331. The fourth C-shaped arm driving mechanism 336 includes a motor and an actuator.

The second base moving mechanism 337 is configured to move the second base 330 mounted on the ceiling along the ceiling to move the overhead traveling C-shaped arm 313 together with the second base 330 in a desired imaging position. The second base moving mechanism 337 is provided inside the second base 330. The second base moving mechanism 337 is configured to include a motor and an actuator.

The control device 340 including the image processing unit 342 has the same configuration as the controller 40 including the image processing unit 42 in the first embodiment, the explanation thereof will be omitted. The image processing unit 342 is configured to generate an image based on detection signals output from the first detector and the second detector 312 of the floor-mounted X-ray imaging unit 301.

(Rotation of Base Side Portion of Second Hose by Second Biasing Unit)

Figure 14:
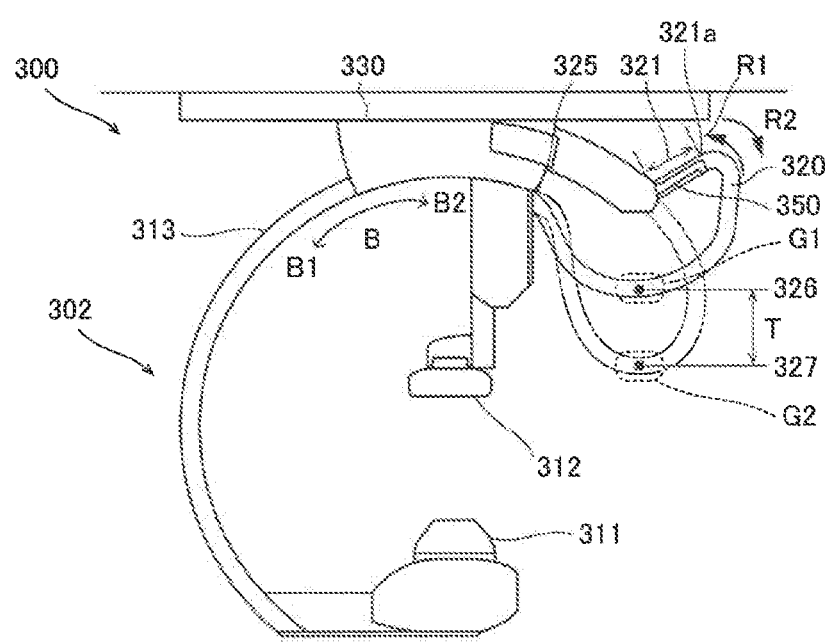
FIG. 14 is Example 2 of a partial perspective view of the X-ray imaging apparatus according to the second embodiment.

With reference to FIG. 9 and FIG. 14, the rotation of the base side portion 321 of the second hose 320 by the second biasing unit 333 in the first rotation direction R1 will be described.

When the overhead traveling C-shaped arm 313 is moved in the circumferential direction (B 1 direction) so that the second detector 312 moves upward to change from the state shown in FIG. 9 to the state shown in FIG. 14, the connection portion 325 of the second hose 320 connected to the overhead traveling C-shaped arm 313 cis arranged above the state shown in FIG. 9 along the circumferential direction of the overhead traveling C-shaped arm 313. The second hose 320 is flexible. Therefore, as shown in FIG. 14, due to the upward movement of the connection portion 325 of the second hose 320 connected to the overhead traveling C-shaped arm 313, in the opposite side portion 322 (see FIG. 9) of the second hose 320, a downward hanging portion G1 is generated according to the action of gravitational force.

In a case where the second biasing unit 333 is not provided (shown by a two-dot chain line), no biasing force for rotating the base side portion 321 in the first rotation direction R1 upward is applied. However, in this embodiment, the second biasing unit 333 (see FIG. 11) applies a biasing force for rotating the base side portion 321 of the second hose 320 in the first rotation direction R1 upward. Therefore, the hanging portion G1 of the second hose 320 is pulled outward and upward of the overhead traveling C-shaped arm 313.

As a result, the position of the most hanging portion 326 of the hanging portion G1 of the second hose 320 becomes a position raised by the distance T than the position of the most hanging portion 327 of the hanging portion G2 of the hose when no second biasing unit 333 is provided (illustrated by the two-dot chain line). Therefore, the hanging amount of the second hose 320 can be reduced as compared with the case where no second biasing unit 333 is provided. Consequently, it is possible to prevent the second hose 320 from coming into contact with the subject or the peripheral device.

Figure 15:
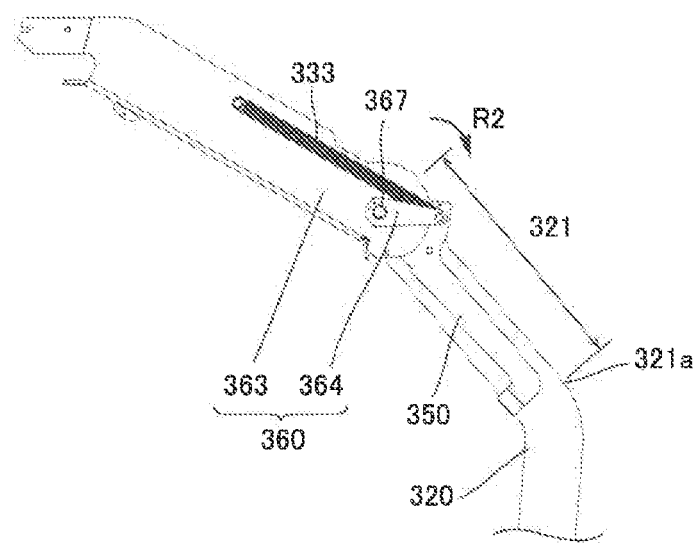
FIG. 15 is a diagram showing another example of the position of the overhead traveling C-shaped arm and the state of a second hose.

Note that in FIG. 9 state, in a case where the overhead traveling C-shaped arm 313 is moved in the circumferential direction (B2 direction) so that the second detector 312 is moved downward, the connection portion 325 of the second hose 320 connected to the overhead traveling C-shaped arm 313 is moved downward from the state shown in FIG. 9. At this time, the distance from the second hose attachment portion 360 to the connection portion 325 also becomes longer. Thus, as shown in FIG. 15, the second shape retention member 350 rotates in the second rotation direction R2 against the biasing force of the second biasing unit 333, and the opposite side 321a of the second hose 320 opposite to the base side portion 321 of is pulled downward. However, the second hose 320 hangs down along the overhead traveling C-shaped arm 313 (see FIG. 9), and therefore, it is possible to prevent the second hose 320 from coming into contact with the subject or the peripheral device.

Note that the second stopper 362 restricts the base side portion 321 of the second hose 320 beyond a predetermined range to downwardly rotate in the second rotation direction R2.

Effects of Second Embodiment

In the second embodiment, the following effects can be obtained.

In the second embodiment, as described above, the C-shaped arm includes both the floor-mounted C-shaped arm 13a supported by the first base 30a mounted on the floor of the examination room 302 and the overhead traveling C-shaped arm 313 supported by the second base 330 mounted on the ceiling, and is provided with a ceiling-mounted X-ray imaging unit 302 including the overhead traveling C-shaped arm 313 sand the floor-mounted X-ray imaging unit 301 including the floor-mounted C-shaped arm 13a.

With this configuration, even in a case where the X-ray imaging apparatus 300 is provided with both the floor-mounted C-shaped arm 13a and the overhead traveling C-shaped arm 313, since the base side portion 21a of the first hose 20a is biased by the first biasing unit 33c to rotate in a first rotation direction R1 away from the outside of floor-mounted C-shaped arm 13a, and the base side portion 321 of the second hose 320 is biased by the second biasing unit 333 to rotate in a first rotation direction R1 away from the outside of the overhead traveling C-shaped arm 313, and therefore, it is possible to suppress the reduction in the distance between the first hose 20a and the second hose 320 and the subject placed on the top board.

Therefore, it is possible to suppress the first hose 20a from coming into contact with the subject placed on the top board in accordance with at least the circumferential movements of the floor-mounted C-shaped arm 13a and the overhead traveling C-shaped arm 313, and it is also possible to suppress the second hose 320 from coming into contact with the subject or the peripheral device.

Further, in the second embodiment, as described above, the second biasing unit 333 biases the base side portion 321 of the second hose 320 in the ceiling-mounted X-ray imaging unit 302 to rotate in the first rotation direction R1 upward. In a case where the connection portion 325 of the second hose 320 connected to the overhead traveling C-shaped arm 313 is moved upward, the opposite side portion 322 of the second hose 320 is pulled outward and upward of the overhead traveling C-shaped arm 313.

Therefore, it is possible to reduce the hanging amount of the hanging portion G1 of the second hose 320 at the opposite side portion 322 of the second hose 320, and therefore, it is possible to further suppress the opposite side of the base side portion 321 of the second hose 320 opposite to the second hose attachment portion 360 from approaching the subject placed on the top board. Therefore, it is possible to further suppress the second hose 320 from coming into contact with the subject and/or the peripheral device.

Further, in the second embodiment, as described above, the second biasing unit 333 biases to rotate the base side portion 321 of the hose 320 upward in the first rotation direction R1 about the rotation shaft 367 extending in the direction along the rotation center line of the overhead traveling C-shaped arm and biases to suppress the base side portion 321 of the second hose 320 to downwardly rotate in the second rotation direction R2 opposite to the first rotation direction R1 about the rotation shaft 367. As a result, it is possible to rotate the base side portion 321 of the second hose 320 about the rotation shaft 367 extending along the rotation center line of the overhead traveling C-shaped arm 313, and therefore, the base side portion 321 of the second hose 320 can be assuredly rotated upwardly in the first rotation direction R1.

Further, in the second embodiment, as described above, the second hose attachment portion 360 includes the root mounting member 363 to which the root of the second hose 320 is attached and the rotation member 364 to which the second biasing unit 333 is connected. The rotation member 364 is rotatably attached to the root mounting member 363 and rotates together with the base side portion 321 of the second hose 320. With this configuration, the rotation member 364 can be assuredly rotated together with the base side portion 321 of the second hose 320 with respect to the root mounting member 363.

Further, in the second embodiment, as described above, the second shape retention member 350 is further provided. In the second shape retention member 350, one end is rotatably connected to the second hose attachment portion 360. The second shape retention member 350 retains the shape of the base side portion 321 of the second hose 320. In the shape retention member 350, when one end is rotated, the other end is rotated in the first rotation direction R1 about the same rotation shaft 367 line as the rotation member 364 together with the base side portion 321 of the second hose 320.

This allows the rotation member 364 and the second shape retention member 350 to rotate integrally in the first rotation direction R1 about the same rotation shaft 367 line together with the base side portion 321 of the second hose 320.

Further, in the second embodiment, as described above, the connection member 368 for connecting the rotation shaft 367 in the rotation member 364, the opposite side end, and the second shape retention member 350 is further provided. The second biasing unit 333 has one end connected to the root mounting member 363 and the other end connected to the connection member 368. This allows the second biasing unit 333 to apply the biasing force to the second shape holding unit and the rotation member 364, and therefore, the second biasing unit 333 can bias the base side portion 321 of the second hose 320 to rotate in the first rotation direction R1 upward.

Further, in the second embodiment, as described above, the second shape retention member 350 is configured to support the outer peripheral surface of the base side portion 321 of the second hose 320. As a result, it is possible to directly rotate the base side portion 321 of the second hose 320 in the first rotation direction R1 upward.

Further, in the second embodiment, as described above, the first stopper 361 is further provided. The first stopper 361 restricts the base side portion 321 of the second hose 3320 to rotate upward in the first rotation direction R1 in a state in which the opposite side of the base side portion 321 of the second hose 320 opposite to the second hose attachment portion 360 is arranged at the upper limit position Q upwardly away from of the overhead traveling C-shaped arm 313 and upward away from the second hose attachment portion 360. With this configuration, in a state in which the second hose 320 is positioned at the upper limit position Q, it is possible to restrict the second shape retention member to further rotate in the first rotation direction R1 by the second biasing unit 333.

Modified Embodiment

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the first and second embodiments described above, an example is shown in which the C-shaped arm 13 is moved in the circumferential direction, but the present invention is not limited thereto. For example, the moving direction or the rotation direction of the C-shaped arm 13 may be in the right oblique (RAO) direction of the subject S or the left oblique (LAO) direction of the subject S. Further, the C-shaped arm 13 may be moved and rotated in a direction combining the circumferential movement and the right oblique (RAO) direction of the subject S or the left oblique (LAO) direction of the subject S.

Further, in the above-described first embodiment, an example is shown in which the biasing unit 33 biases the base side portion 21 of the hose 20 to rotate in first rotation direction R1 about the central axis 61 of the hose attachment portion 60, but the present invention is not limited thereto. For example, the biasing unit 33 may be configured to bias the base side portion 21 of the hose 20 to rotate about an axis perpendicular to the central axis 61 of the hose attachment portion 60.

Further, in the above-described first embodiment, an example is shown in which the base side portion 21 of the hose 20 is formed to extend along the central axis 61 of the hose attachment portion 60 from the hose attachment portion 60 and extend obliquely with respect to the central axis 61 of the hose attachment portion 60 at the opposite side of the hose attachment portion 60, but the present invention is not limited thereto. For example, the base side portion 21 of the hose 20 may be formed to extend obliquely with respect to the central axis 61 of the hose attachment portion 60.

Further, in the above-described first embodiment, an example is shown in which the opposite side of the base side portion 21 of the hose 20 opposite to the hose attachment portion 60 is arranged at the outside limit position P outwardly away from the C-shaped arm than the hose attachment portion 60, but the present invention is not limited thereto. For example, the opposite side of the base side portion 21 of the hose 20 opposite to the hose attachment portion 60 may be arranged inside the C-shaped arm 13 than the hose attachment portion 60.

Further, in the above-described first embodiment, an example is shown in which the shape retention member 50 is inserted into the base side portion 21 of the hose 20 to retain the shape of the base side portion 21 of the hose, but the present invention is not limited thereto. It may be configured such that for example, without using the shape retention member 50, the base side portion 21 of the hose 20 is formed of a material large in stiffness, and thus is difficult to deform. Further, the hose attachment portion 60 may be formed such that the part thereof protrudes outward without using the shape retention member 50, so that it is difficult to deform.

In the above-described first embodiment, an example is shown in which the shape retention member 50 is formed of a metal rod-shaped member, but the present invention is not limited thereto. For example, the shape retention member 50 may be made of resin instead of metal, or may be made of a tubular member instead of a rod-shaped member.

In the above-described first embodiment, an example is shown in which the biasing unit 33 is composed of the tension spring 33a and the wire 33b, but the present invention is not limited thereto. For example, the biasing unit 33 may be configured by a torsion spring or a spiral spring.

Further, although in the first embodiment, an example is shown in which it is provided with the cover 34 covering the biasing unit 33, the present invention is not limited thereto. The biasing unit 33 may not be covered by the cover 34.

Further, in the above-described first embodiment, an example is shown in which the biasing unit 33 is provided on the base 30, but the present invention is not limited thereto. For example, the biasing unit 33 may be provided to other than the base 30, or may be provided independently.

Further, in the above-described first embodiment, an example is shown in which the hose attachment portion 60 includes the inner cylindrical portion 62, and the root of the shape retention member 50 is connected to the inner cylindrical portion 62 of the hose attachment portion 60, but the present invention is not limited thereto. For example, the shape retention member 50 may include the inner cylindrical portion 62 at the root of the shape retention member 50, and the inner cylindrical portion 62 of the shape retention member 50 may be connected to the outer cylindrical portion 63 of the hose attachment portion 60.

Further, in the above-described first embodiment, an example is shown in which the base side portion 21 of the hose 20 is configured not to be easily deformed, but the present invention is not limited thereto. For example, the base side portion 21 of the hose 20 may not be configured to be hard to deform.

Further, in the above-described first embodiment, an example is shown in which the X-ray imaging apparatus 100 is an X-ray imaging apparatus provided with the floor-mounted C-shaped arm, but the present invention is not limited thereto. For example, the X-ray imaging apparatus may be an X-ray imaging apparatus provided with an overhead traveling C-shaped arm.

Further, in the above-described second embodiment, an example is shown in which the second biasing unit 333 biases the base side portion 321 of the second hose 320 to rotate upward in the first rotation direction R1, but the present invention is not limited thereto. For example, the second biasing unit 333 may be configured to bias the base side portion 321 of the second hose 320 to rotate outwardly and upwardly away from the overhead traveling C-shaped arm 313.

Further, in the second embodiment, an example is shown in which the connection member 368 for connecting the rotation member 364 and the second shape retention member 350 is further provided, but the present invention is not limited thereto. For example, it may be configured such that the connection member 368 is not provided, and the other end of the second biasing unit 333 is connected to the second hose 320.

Further, in the above-described second embodiment, an example is shown in which the second shape retention member 350 holds the shape of the base side portion 321 of the second hose 320, but the present invention is not limited thereto. It may be configured such that without using the second shape retention member 350, for example, the base side portion 321 of the second hose 320 is formed of a material having a rigidity large than that of the opposite side portion 322 to be difficult to deform.

Further, in the above-described second embodiment, an example is shown in which the second shape retention member 350 is configured to support the outer peripheral surface of the base side portion 321 of the second hose 320, but the present invention is not limited thereto. For example, the second shape retention member 350 may be configured to extend the inside of the base side portion 321 of the second hose 320 to retain the shape of the base side portion 321 of the second hose 320 from the inside of the second hose 320.

Further, in the second embodiment, an example is shown in which the first stopper 361 and the second stopper 362 are provided, but the present invention is not limited thereto. For example, the first stopper 361 and the second stopper 362 may not be provided. For example, in a case where the first stopper 361 is not provided, the spring constant of the second biasing unit 333 may be set such that the position of the balance between the tensile force of the second biasing unit 333 as a tension spring and the force in the second rotation direction R2 applied to the second shape retention member 350 is at the upper limit position Q.

Further, in the above-described second embodiment, an example is shown in which the root mounting member 363 includes the member first portion 365 and the member second portion 366, but the present invention is not limited thereto. For example, the root mounting member 363 may not be provided with either one of the member first portion 365 and the member second portion 366, and the configuration of the root mounting member 363 is not particularly limited.

[Aspects]

It will be understood by those skilled in the art that the above-described exemplary embodiments are concrete examples of the following aspects.

(Item 1)

An X-ray imaging apparatus comprising:
- an X-ray source;
- a detector configured to detect X-rays emitted from the X-ray source;
- a C-shaped arm configured to support the X-ray source and the detector;
- a hose configured to accommodate wiring connected to at least one of the X-ray source and the detector, the hose including a base side portion and an opposite side portion connected to the C-shaped arm on an opposite side of the base side portion;
- a base including a C-shaped arm support portion rotatably supporting the C-shaped arm and a hose attachment portion to which the base side portion of the hose is rotatably attached;
- a biasing unit configured to bias the base side portion of the hose to rotate about the hose attachment portion in a first rotation direction away from an outside of the C-shaped arm; and an image processing unit configured to generate an image based on a detection signal output from the detector.

(Item 2)

The X-ray imaging apparatus as recited in claim 1,
wherein the base side portion of the hose is formed to extend along a central axis of the hose attachment portion from the hose attachment portion and is formed to extend obliquely with respect to the central axis of the hose attachment portion on an opposite side of the hose attachment portion, and
wherein the biasing unit biases base the side portion of the hose to rotate in the first rotation direction about the central axis of the hose attachment portion.

(Item 3)

The X-ray imaging apparatus as recited in the above-described Item 1 or 2,
wherein an opposite side of the base side portion of the hose opposite to the hose attachment portion is arranged at an outside limit position outwardly away from the C-shaped arm than the hose attachment portion, and
wherein the biasing unit biases the base side portion of the hose to suppress a rotation of the base side portion in a second rotation direction opposite to the first rotation direction in accordance with a movement of the opposite side of the hose toward an inner side of the C-shaped arm.

(Item 4)

The X-ray imaging apparatus as recited in any one of the above-described Items 1 to 3,
wherein the base side portion of the hose is configured to be hard to deform.

(Item 5)

The X-ray imaging apparatus as recited in claim 1, further comprising:
a shape retention member having a root connected to the hose attachment portion, the shape retention member extending an inside of the base side portion of the hose to retain a shape of the base side portion of the hose, a tip end side of the shape retention member being rotated in the first rotation direction together with the base side portion of the hose when the root is rotated by the biasing unit.

(Item 6)

The X-ray imaging apparatus as recited in the above-described Item 5
wherein the shape retention member is formed to extend from the hose attachment portion along a central axis of the hose attachment portion, the tip end side being formed to extend obliquely with respect to the central axis of the hose attachment portion.

(Item 7)

The X-ray imaging apparatus as recited in the above-described Item 5 or 6,
wherein the shape retention member is made of a metal rod-shaped member.

(Item 8)

The X-ray imaging apparatus as recited in any one of the above-described Items 1 to 7,
wherein the biasing unit is provided on the base.

(Item 9)

The X-ray imaging apparatus as recited in the above-described Item 8, further comprising:
a cover provided on the base to cover the biasing unit.

(Item 10)

The X-ray imaging apparatus as recited in any one of the above-described Items 1 to 9,
wherein the biasing unit includes a tension spring and a wire in having one end connected to the tension spring and the other end connected to the hose attachment portion.

(Item 11)

The X-ray imaging apparatus as recited in the above-described Item 10,
wherein the tension spring biases the base side portion of the hose to rotate in the first rotation direction by rotating the hose attachment portion via the wire.

(Item 12)

The X-ray imaging apparatus as recited in any one of the above-described Items 1 to 11,
wherein the C-shaped arm is configured to be a floor-mounted C-shaped arm supported by the base mounted on a floor of an examination room or an overhead traveling C-shaped arm supported by the base mounted on a ceiling of the examination room.

(Item 13)

The X-ray imaging apparatus as recited in the above-described Item 1,
wherein the C-shaped arm includes both a floor-mounted C-shaped arm supported by the base mounted on a floor of an examination room and an overhead traveling C-shaped arm supported by the base mounted on a ceiling of the examination room, and
wherein the C-shaped arm includes a ceiling-mounted X-ray imaging unit including the overhead traveling C-shaped arm and a floor-mounted X-ray imaging unit including the floor-mounted C-shaped arm.

Item 14

The X-ray imaging apparatus as recited in the above-described Item 13,
wherein the biasing unit biases the base side portion of the hose in the ceiling-mounted X-ray imaging unit to rotate in the first rotation direction upward.

Item 15

The X-ray imaging apparatus as recited in the above-described Item 14,
wherein the biasing unit biases the base side portion of the hose to rotate about a rotation axis extending in a direction along a rotation center line of the overhead traveling C-shaped arm in the first rotation direction upward, and biases the base side portion of the hose to suppress a rotation of the base side portion about the rotation axis in a second rotation direction opposite to the first rotation direction downward.

Item 16

The X-ray imaging apparatus as recited in the above-described Item 15,
wherein the hose attachment portion includes a root mounting member to which a root of the hose is attached and a rotation member to which the biasing unit is connected, the rotation member being rotatably attached to the root mounting member to rotate together with the base side portion of the hose.

Item 17

The X-ray imaging apparatus as recited in the above-described Item 16, further comprising:
a shape retention member, the shape retention member having one end rotatably connected to the hose attachment portion, the shape retention member holding a shape of the base side portion of the hose, the other end side being rotated in the first rotation direction about the same rotation axis as the rotation member together with the base side portion of the hose when the one end is rotated.

Item 18
The X-ray imaging apparatus as recited in the above-described Item 17, further comprising:
a connection member configured to connect an end of the rotation member on an opposite side of the rotation shaft and the shape retention member,
wherein the biasing unit has one end connected to the root mounting member and the other end connected to the connection member.

Item 19
The X-ray imaging apparatus as recited in the above-described Item 17,
wherein the shape retention member is configured to support an outer peripheral surface of the base side portion of the hose.

Item 20
The X-ray imaging armor as recited in the above-described Item 14, further comprising:
a stopper configured to restrict a rotation of the base side portion of the hose in the first rotation direction upward in a state in which the opposite side of the base side portion of the hose opposite to the hose attachment portion is positioned at an upper limit position away from the overhead traveling C-shaped arm outward than the hose attachment portion and away from the hose attachment portion upward.

The invention claimed is:

1. An X-ray imaging apparatus comprising:
an X-ray source;
a detector configured to detect X-rays emitted from the X-ray source;
a C-shaped arm configured to support the X-ray source and the detector;
a hose configured to accommodate wiring connected to at least one of the X-ray source and the detector, the hose including a base side portion and an opposite side portion connected to the C-shaped arm on an opposite side of the base side portion;
a base including a C-shaped arm support portion rotatably supporting the C-shaped arm and a hose attachment portion to which the base side portion of the hose is rotatably attached;
a biasing unit configured to bias the base side portion of the hose to rotate about the hose attachment portion in a first rotation direction outwardly away from the C-shaped arm; and
an image processing unit configured to generate an image based on a detection signal output from the detector.

2. The X-ray imaging apparatus as recited in claim 1,
wherein the base side portion of the hose is formed to extend from the hose attachment portion along a central axis of the hose attachment portion and is formed to extend obliquely with respect to the central axis of the hose attachment portion on an opposite side of the hose attachment portion, and
wherein the biasing unit biases the base side portion of the hose to rotate about the central axis of the hose attachment portion in the first rotation direction.

3. The X-ray imaging apparatus as recited in claim 1,
wherein an opposite side of the base side portion of the hose opposite to the hose attachment portion is arranged at an outside limit position outwardly away from the C-shaped arm than the hose attachment portion, and
wherein the biasing unit biases the base side portion of the hose to suppress a rotation of the base side portion in a second rotation direction opposite to the first rotation direction in accordance with a movement of the opposite side of the hose toward an inner side of the C-shaped arm.

4. The X-ray imaging apparatus as recited in claim 1,
wherein the base side portion of the hose is configured to be hard to deform.

5. The X-ray imaging apparatus as recited in claim 1, further comprising:
a shape retention member having a root connected to the hose attachment portion, the shape retention member extending an inside of the base side portion of the hose to retain a shape of the base side portion of the hose, a tip end side of the shape retention member being rotated in the first rotation direction together with the base side portion of the hose when the root is rotated by the biasing unit.

6. The X-ray imaging apparatus as recited in claim 5
wherein the shape retention member is formed to extend from the hose attachment portion along a central axis of the hose attachment portion, the tip end side being formed to extend obliquely with respect to the central axis of the hose attachment portion.

7. The X-ray imaging apparatus as recited in claim 5,
wherein the shape retention member is made of a metal rod-shaped member.

8. The X-ray imaging apparatus as recited in claim 1,
wherein the biasing unit is provided on the base.

9. The X-ray imaging apparatus as recited in claim 8, further comprising:
a cover provided on the base to cover the biasing unit.

10. The X-ray imaging apparatus as recited in claim 1,
wherein the biasing unit includes a tension spring and a wire, the wire having one end connected to the tension spring and the other end connected to the hose attachment portion.

11. The X-ray imaging apparatus as recited in claim 10,
wherein the tension spring biases the base side portion of the hose to rotate in the first rotation direction by rotating the hose attachment portion via the wire.

12. The X-ray imaging apparatus as recited in claim 1,
wherein the C-shaped arm is configured to be a floor-mounted C-shaped arm supported by the base mounted on a floor of an examination room or an overhead traveling C-shaped arm supported by the base mounted on a ceiling of the examination room.

13. The X-ray imaging apparatus as recited in claim 1,
wherein the C-shaped arm includes both a floor-mounted C-shaped arm supported by the base mounted on a floor of an examination room and an overhead traveling C-shaped arm supported by the base mounted on a ceiling of the examination room, and
wherein the C-shaped arm includes a ceiling-mounted X-ray imaging unit including the overhead traveling C-shaped arm and a floor-mounted X-ray imaging unit including the floor-mounted C-shaped arm.

14. The X-ray imaging apparatus as recited in claim 13,
wherein the biasing unit biases the base side portion of the hose in the ceiling-mounted X-ray imaging unit to rotate in the first rotation direction upward.

15. The X-ray imaging apparatus as recited in claim 14,
wherein the biasing unit biases the base side portion of the hose to rotate about a rotation axis extending in a direction along a rotation center line of the overhead traveling C-shaped arm in the first rotation direction upward, and biases the base side portion of the hose to suppress a rotation of the base side portion about the rotation axis in a second rotation direction opposite to the first rotation direction downward.

16. The X-ray imaging apparatus as recited in claim 15, wherein the hose attachment portion includes a root mounting member to which a root of the hose is attached and a rotation member to which the biasing unit is connected, the rotation member being rotatably attached to the root mounting member to rotate together with the base side portion of the hose.

17. The X-ray imaging apparatus as recited in claim 16, further comprising:
a shape retention member, the shape retention member having one end rotatably connected to the hose attachment portion, the shape retention member holding a shape of the base side portion of the hose, the other end side being rotated in the first rotation direction about the same rotation axis as the rotation member together with the base side portion of the hose when the one end is rotated.

18. The X-ray imaging apparatus as recited in claim 17, further comprising:
a connection member configured to connect an end of the rotation member on an opposite side of the rotation shaft and the shape retention member,
wherein the biasing unit has one end connected to the root mounting member and the other end connected to the connection member.

19. The X-ray imaging apparatus as recited in claim 17, wherein the shape retention member is configured to support an outer peripheral surface of the base side portion of the hose.

20. The X-ray imaging armor as recited in claim 14, further comprising:
a stopper configured to restrict a rotation of the base side portion of the hose in the first rotation direction upward in a state in which the opposite side of the base side portion of the hose opposite to the hose attachment portion is positioned at an upper limit position away from the overhead traveling C-shaped arm outward than the hose attachment portion and away from the hose attachment portion upward.

* * * * *